United States Patent [19]
McGann

[11] Patent Number: 5,115,799
[45] Date of Patent: May 26, 1992

[54] OCCLUSAL LIP AND CHEEK RETRACTOR

[76] Inventor: Benson D. McGann, 15 N. Vista de Catalina, South Laguna, Calif. 92677

[21] Appl. No.: 641,654

[22] Filed: Jan. 15, 1991

[51] Int. Cl.$^5$ ............................................. A61B 1/00
[52] U.S. Cl. .................................... 128/12; 433/140
[58] Field of Search ...................... 433/93, 136, 140; 128/12, 13, 14, 20

[56] References Cited

U.S. PATENT DOCUMENTS

| | | | |
|---|---|---|---|
| 903,344 | 11/1908 | Wackler | 433/140 |
| 3,916,879 | 11/1975 | Cotten | 128/12 |
| 4,053,984 | 10/1977 | Moss | 433/93 |
| 4,200,089 | 4/1980 | Inoue | 128/12 |

Primary Examiner—Cary E. O'Connor

[57] ABSTRACT

A lip and cheek retracting device formed from a rigid sheet of autoclavable material. A first pair of opposing prongs with a first space formed therebetween extends in the opposite direction of a second pair of opposing prongs with a second spaced formed similarly therebetween. The first pair of prongs are shaped to fit around an adult's gum ridge, and the second pair of prongs are shaped to fit around a child's gum ridge. An indented curvature formed in each portion of the peripheral edge lying between one prong of the first pair of opposing prongs and one prong of the second pair of opposing prongs is used for manually holding the device in place during use.

5 Claims, 2 Drawing Sheets

OCCLUSAL LIP AND CHEEK RETRACTOR

FIELD OF THE INVENTION

The invention relates to the field of dental devices used to improve access to the mouth interior. More specifically, this invention relates to lip and cheek retractors that allow a clear view of the occlusal surface of the teeth.

BACKGROUND OF THE INVENTION

When undergoing a dental procedure it is obviously necessary for a patient to maintain an opened-mouth position to allow the dental professional access to the mouth. Frequently, however, the patient cannot maintain such a position for the duration of the procedure because of muscle fatigue, or, simply cannot expose those areas of his mouth that are the subject of the procedure, especially if unconscious. Accordingly, a variety of devices have been created to assist in maintaining a lip and cheek retracted and opened—mouth position.

Many of these retraction devices, however, obscure the view of the occlusal (biting) surfaces of the teeth. This is a drawback to the dental professional who is interested in obtaining an unobscured view of the occlusal surfaces of the teeth, as, for example, when photographing these surfaces. Other devices retract the cheeks in a lateral fashion, which prevents the mouth from opening fully and consequently hinders a full view of the occlusal surfaces of the teeth of both the upper or lower jaw.

One retracting device, taught in U.S. Pat. No. 4,053,984 to Moss, forces the mouth open from the inside through use of an upper and lower U-shaped tubular frame. Cheek deflectors are removably secured between these U-shaped frames and are outwardly concave in shape. This device succeeds in exposing the occlusal (or biting) surfaces of the teeth, provided that the disclosed tongue depressor is detached from the device. However, as this device retracts both the upper and lower lips and cheeks of the patient simultaneously, neither the upper or lower lips and cheeks are fully retracted; rather, both the upper and lower lips and cheeks are retracted only a portion of the distance that they could be retracted separately. Further, this device is complex in that it is intricately designed to assist in the removal of saliva from the patient's mouth when disposed therein; such complexity necessarily dictates a relatively high manufacturing cost. Still further, the device is not autoclavable, and must be cold sterilized. Thus, this device is expensive for the dental professional to use for relatively quick photographic applications, and is ill-suited for obtaining a full view of either the upper or lower occlusal surfaces of the teeth separately.

Clearly, then, there is a need for a device that permits the occlusal surfaces of the teeth of either the upper or lower jaw to be fully exposed, in autoclavable, and is relatively inexpensive to manufacture.

SUMMARY OF THE INVENTION

The present invention is a dental lip and cheek retractor comprising two pairs of prongs formed from a thin but rigid sheet of autoclavable material, one pair of prongs being larger than the other pair. The space formed between the larger pair of prongs is larger than the space formed between the smaller pair of prongs, and is approximate in shape and size to the exterior of the gum ridge from the left to right side of an adult's mouth. The smaller space formed between the smaller pair of prongs is approximate in shape and size to the exterior of the gum ridge from the left to right side of a child's mouth. An indented curvature suitable for gasping is formed between the two pairs of prongs on the peripheral edge of the device.

In use, one pair of prongs is chosen as appropriate for the mouth size of the patient. This pair of prongs is inserted into the mouth of the patient such that the prongs lie on the exterior side of the gum ridge from the left to right side of the patient's mouth. The dental professional or the patient then raises or lowers the retraction device, thereby retracting either the upper or lower lips and cheeks, respectively, from the occlusal areas of the teeth. The dental professional, or the patient himself, then holds the device in place for the duration of the dental procedure, grasping either the unused set of prongs or the indented curvature.

This invention succeeds in fully exposing either the upper or lower occlusal surfaces of a patient's teeth, and is suitable for a variety of mouth sizes. The device can be stamped from a sheet, extruded, or injection molded, all from autoclavable material. Consequently, it is far less costly to manufacture than prior lip and cheek retractors and may therefore be used only once, i.e., disposed of rather than being being sterilized for reuse. This is an attractive feature for any dental product because the fear of contracting the AIDS virus and other diseases discourages the reuse of such products.

Other features and advantages of the present invention will become apparent from the following more detailed description, taken in conjunction with the accompanying drawings, which illustrate, by way of example, the principles of the invention.

DESCRIPTION OF THE DRAWINGS

The accompanying drawings illustrate the invention. In such drawings.

DETAILED DESCRIPTION OF THE INVENTION

Figure 1:
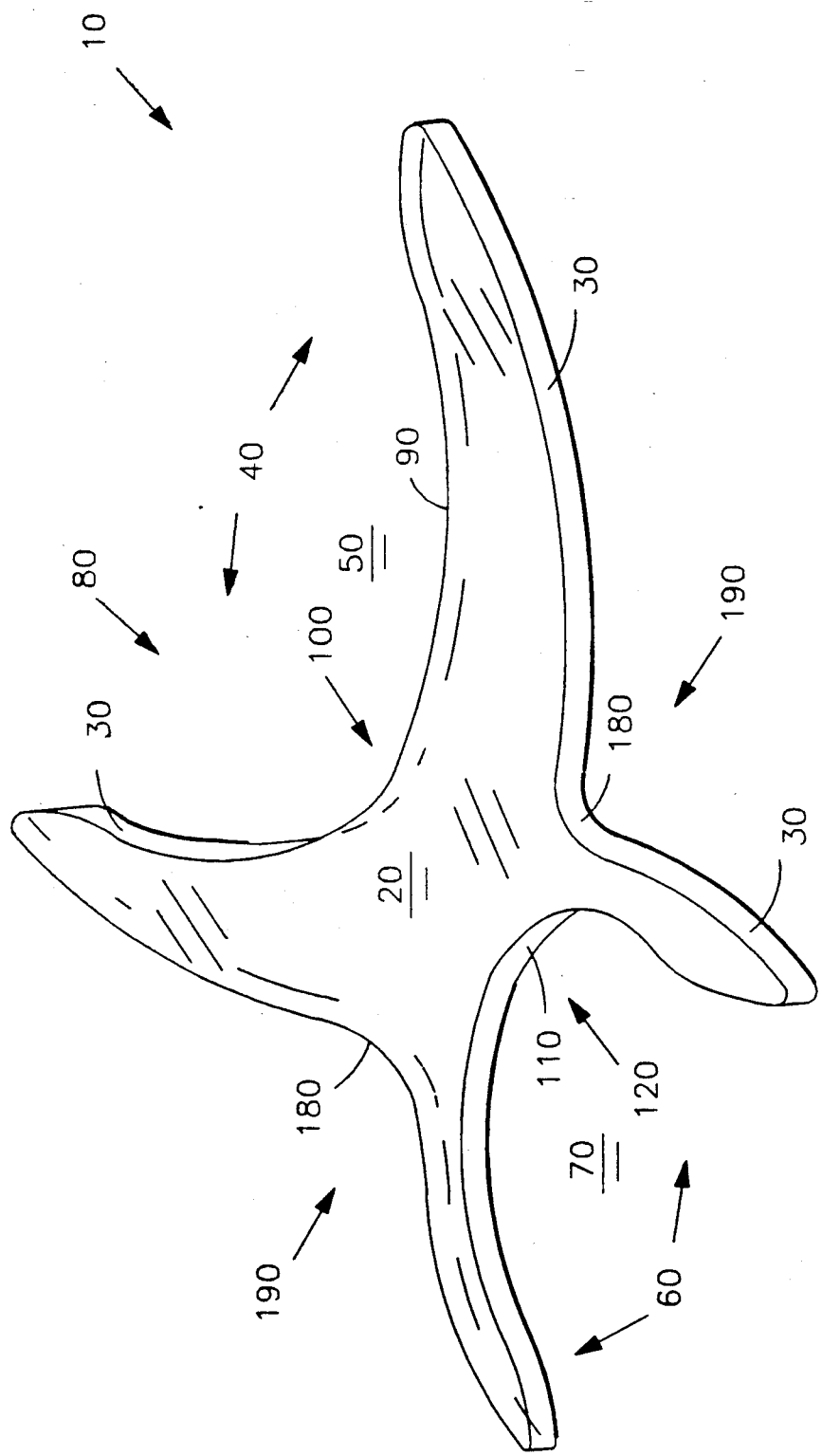
FIG. 1 is a top plan view of the invention.
Figure 2:
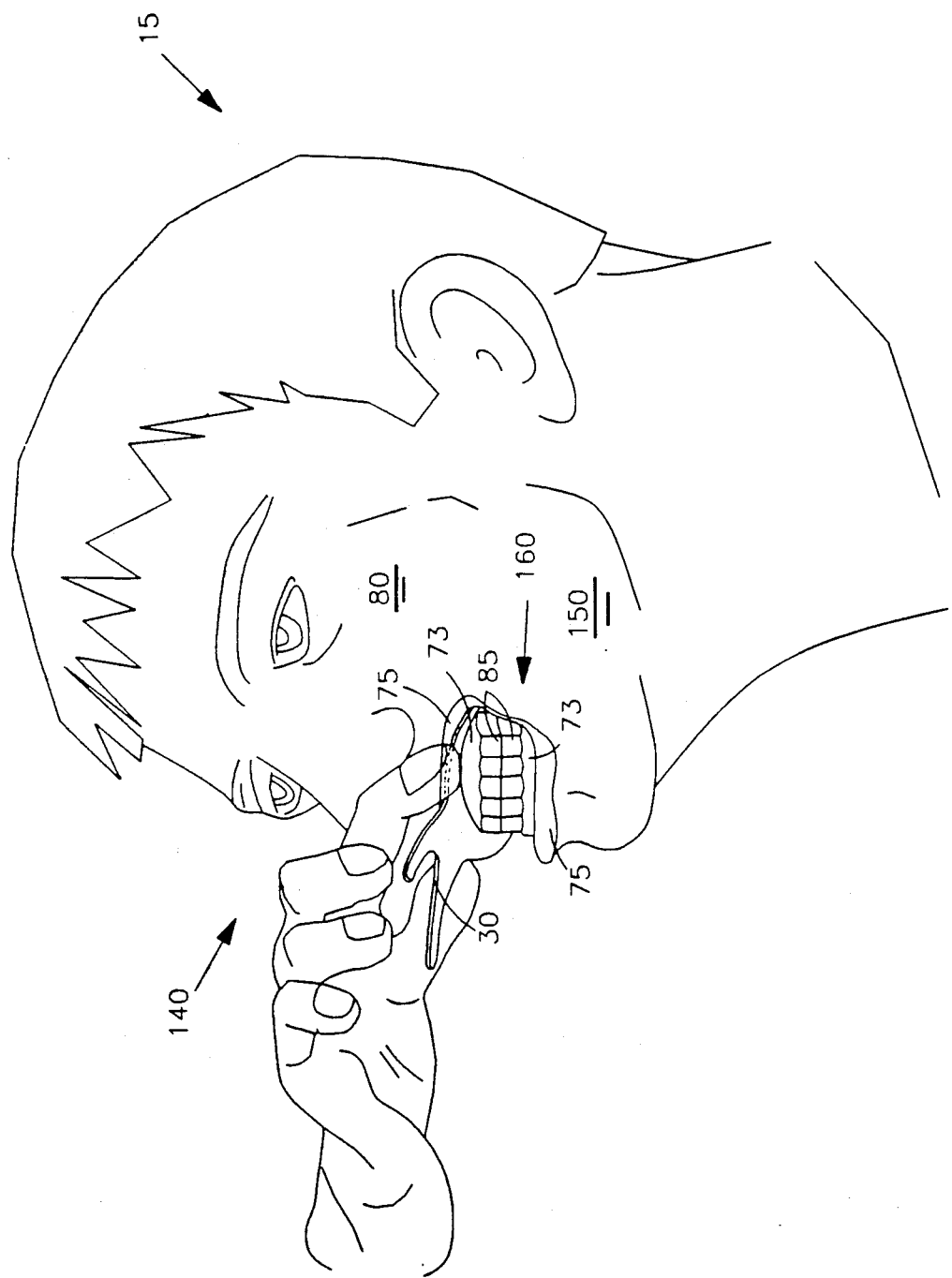
FIG. 2 is a perspective view of the invention placed within a person's mouth, as in normal use.

FIGS. 1 and 2 show a dental lip and cheek retracting device 10 comprising a rigid sheet 20 having a peripheral edge 30. The rigid sheet 20 may be of any clear or colored autoclavable, rigid material. The peripheral edge 30 forms a first pair of opposing prongs 40 with a first space 50 formed therebetween. The peripheral edge 30 also forms a second pair of opposing prongs 60 with a second space 70 formed therebetween. The first pair of prongs 40 is larger than the second pair of prongs 60. Likewise, the first space 50 is larger than the second space 70. The first pair of opposing prongs 40 and the second pair of opposing prongs 60 extend in opposite directions. The first pair of opposing prongs 40 and the second pair of opposing prongs 60 each form a desirable shape for pushing the lips 75 and cheeks 80 away from the teeth 85 in order to expose the teeth 85 and gums 73 of the patient 15.

In one embodiment of the invention, a first portion 90 of the peripheral edge 30 lying between the first pair of opposing prongs 40 forms a first curved arch 100. Likewise, a second portion 110 of the peripheral edge 30 lies between the second pair of opposing prongs 60 and defines a second curved arch 120. The first portion 90 of the peripheral edge 30 conformably fits the exterior of gums 73 from a left side 140 to a right 150 of a mouth 160 of an adult. Likewise, the second portion 110 of the peripheral edge 30 fits over comparable surfaces of a small adult or child. Further, an indented curvature 190 is formed in each side portion 180 of the peripheral edge 30 lying between the first pair of opposing prongs 40 and the second pair of opposing prongs 60 for convenient manual grasping of the retracting device 10 while in use.

In use, either the first pair of opposing prongs 40 or the second pair of opposing prongs 60 is selected as appropriate for the size of the gums 73 of the patient 15. In the case where the patient 15 has a relatively large mouth 160, the first pair of opposing prongs 40 is chosen and inserted into the mouth 160 of the patient 15 such that the first pair of opposing prongs 40 lie on the exterior sides of the gums 73 from the left side 140 to the right side 150 of the mouth 160 of the patient 15. The lip and cheek retracting device 10 is then either lifted up until the teeth 85 of an upper jaw of the patient 15 are exposed, or pressed down until the teeth 85 of a lower jaw of the patient 15 are exposed. Either the patient 15 or a dental professional can grasp the lip and cheek retracting device 10 at the indented curvatures 190 in order to hold the lip and cheek retracting device 10 in place during the procedure.

For a small mouth the second pair of opposing prongs 60 is chosen, and the operation of the lip and cheek retracting device 10 is similar to that described above except that the second pair of opposing prongs 60 is inserted into the mouth 160 of the patient 15 instead of the first pair of opposing prongs 40.

While the invention has been described with reference to a preferred embodiment, it is to be clearly understood by those skilled in the art that the invention is not limited thereto. For example, the first pair of opposing prongs 40 and the second pair of opposing prongs 60 could be sized and shaped such that one pair is more appropriate for the upper jaw of the patient 15, and the other pair is more appropriate for the lower jaw of the patient 15. Thus, the scope of the invention is to be interpreted only in conjunction with the appended claims.

What is claimed is:

1. A dental lip and cheek retracting device comprising:

a rigid sheet having a peripheral edge, the peripheral edge forming a first pair of opposing prongs with a first space formed between said prongs, the peripheral edge also forming a second pair of opposing prongs with a second space formed between said second pair of opposing prongs, the first pair of prongs being larger than the second pair of prongs, the first space being larger than the second space, the first and second pairs of opposing prongs extending in opposite directions, each pair of opposing prongs forming a surface for pushing the lips and cheeks away from the teeth in order to expose the teeth and gums.

2. The device of claim 1 wherein a first portion of the peripheral edge lying between the first pair of opposing prongs forms a first curved arch, a second portion of the peripheral edge which lies between the second pair of opposing prongs defines a second curved arch.

3. The device of claim 2 wherein the first portion of the peripheral edge fits an approximate shape of the exterior of the gum ridge from the left side to the right side of an adult mouth.

4. The device of claim 2 wherein the second portion of the peripheral edge fits an approximate shape of the exterior of the gum ridge from the left side to the right side of a child's mouth.

5. The device of claim 1 wherein each portion of the peripheral edge lying between one prong of the first pair and one prong of the second pair of opposing prongs forms an indented curvature, said indented curvature forming a convenient place for manually grasping the device in use.

* * * * *